(12) United States Patent
Drobe

(10) Patent No.: US 9,763,568 B2
(45) Date of Patent: Sep. 19, 2017

(54) METHOD OF EVALUATING THE EFFICIENCY OF A MYOPIA CONTROL PRODUCT

(71) Applicant: ESSILOR INTERNATIONAL (COMPAGNIE GENERALE D'OPTIQUE), Charenton-le-Pont (FR)

(72) Inventor: Björn Drobe, Singapore (SG)

(73) Assignee: ESSILOR INTERNATIONAL (COMPGNIE GENERALE D'OPTIQUE), Charenton-le-Pont (FR)

( * ) Notice: Subject to any disclaimer, the term of this patent is extended or adjusted under 35 U.S.C. 154(b) by 0 days.

(21) Appl. No.: 14/770,031

(22) PCT Filed: Feb. 26, 2014

(86) PCT No.: PCT/EP2014/053710
§ 371 (c)(1),
(2) Date: Aug. 24, 2015

(87) PCT Pub. No.: WO2014/131791
PCT Pub. Date: Sep. 4, 2014

(65) Prior Publication Data
US 2016/0000314 A1    Jan. 7, 2016

(30) Foreign Application Priority Data

Mar. 1, 2013  (EP) ..................................... 13305241

(51) Int. Cl.
| A61B 3/00 | (2006.01) |
| G02C 7/00 | (2006.01) |
| A61B 3/028 | (2006.01) |
| A61B 3/10 | (2006.01) |
| A61B 3/103 | (2006.01) |

(52) U.S. Cl.
CPC ............ *A61B 3/0025* (2013.01); *A61B 3/028* (2013.01); *A61B 3/103* (2013.01); *A61B 3/1005* (2013.01); *G02C 7/00* (2013.01); *G02C 2202/24* (2013.01)

(58) Field of Classification Search
CPC .................................................. G02C 2202/24
USPC ............................................................ 351/246
See application file for complete search history.

(56) References Cited

PUBLICATIONS

J.J. Wahine et at, "Interventions to slow progression of myopia in children", Cochrane Database of Systematic Reviews, pp. 1-125, XP055068082, Jan. 1, 2011 http://onlinelibrary.wiley.com/store/10.1002/14651858.CD004916.pub3/asset/CD004916.
X. Zhu, "In a Matter of Minutes, the Eye Can Know Which Way to Grow", Investigative Ophthalmology & Visual Science, vol. 46, No. 7, Jul. 1, 2005, pp. 2238-2241, XP055068042.

*Primary Examiner* — Mahidere Sahle
(74) *Attorney, Agent, or Firm* — Oblon, McClelland, Maier & Neustadt, L.L.P.

(57) ABSTRACT

A method of evaluating the efficiency of a myopia control product for a wearer, the method comprising: an initial myopia indicator providing step S1, during which the initial value of a myopia indicator of the wearer is provided, a myopia condition step S2, during which the wearer using the myopia control product is placed in myopia inducing conditions, a resulting myopia indicator determining step S3, during which the resulting value of the myopia indicator of the wearer is determined after the wearer has been placed in the myopia inducing conditions, an efficiency evaluation step S4, during which the efficiency of the myopia control product is evaluated by comparing the initial value of the myopia indicator and the resulting value of the myopia indicator.

15 Claims, 2 Drawing Sheets

METHOD OF EVALUATING THE EFFICIENCY OF A MYOPIA CONTROL PRODUCT

RELATED APPLICATIONS

This is a U.S. national stage application under 35 USC §371 of application No. PCT/EP2014/053710, filed on Feb. 26, 2014. This application claims the priority of European application no. 13305241.5 filed Mar. 1, 2013, the entire content of which is hereby incorporated by reference.

FIELD OF THE INVENTION

The invention relates to a method of evaluating the efficiency of a myopia control product for a wearer and a method for selecting a myopia control product for a wearer among a list of myopia control products.

BACKGROUND OF THE INVENTION

The discussion of the background of the invention herein is included to explain the context of the invention. This is not to be taken as an admission that any of the material referred to was published, known or part of the common general knowledge at the priority date of any of the claims.

It has been observed that some individuals, in particular children, focus inaccurately when they observe an object which is situated at a short distance away, that is to say, in near vision conditions. Because of this focusing defect on the part of a myopic child which is corrected for his far vision, the image of an object close by is also formed behind his retina, even in the foveal area.

Many type of products for slowing down myopia progression can be used, such as ophthalmic lenses, contact lenses or drugs.

For example, to avoid a myopia progression which is due to such focusing defect, it is known to use a myopia-correcting lens which is of the progressive multifocal ophthalmic lens type. An example of such progressive multifocal ophthalmic lens is disclosed in U.S. Pat. No. 6,343,861.

Bifocal lenses may also be an example of ophthalmic lenses that can be used to slow down myopia progression.

Each individual may react differently to the different myopia control products. However, since myopia progression is a long term process it is difficult for an eye care professional to estimate the efficiency of a given myopia control product for a wearer.

SUMMARY OF THE INVENTION

One object of the present invention is to provide a method for evaluating the efficiency of a myopia control product on the long term for a given wearer.

In accordance with a first aspect of the invention there is provided a method of evaluating the efficiency of a myopia control product for a wearer. The method comprises:
  an initial myopia indicator providing step, during which the initial value of a myopia indicator of the wearer is provided,
  a myopia condition step, during which the wearer using a myopia control product is placed in myopia inducing conditions,
  a resulting myopia indicator determining step, during which the resulting value of the myopia indicator of the wearer is determined after the wearer has been placed in the myopia inducing conditions,
  an efficiency evaluation step, during which the efficiency of the myopia control product is evaluated by comparing the initial value of the myopia indicator and the resulting value of the myopia indicator.

Advantageously, having the wearer placed in myopia inducing conditions allows an eye care professional to evaluate within a few minutes the efficiency on the long term of a myopia control product for a given wearer. Indeed, having the wearer in myopia inducing conditions induces a rapid and quantifiable change of the value of the myopia indicator.

Furthermore, the method according to the invention may help the eye care professional demonstrate the efficiently of a myopia control product to the wearer.

According to further embodiments which can be considered alone or in combination:
  the myopia indicator is a parameter related to the axial length of the wearer's eyes or the thickness of the wearer's choroid; and/or
  the myopia control product is the wearer's usual distance correction; and/or
  the myopia inducing conditions are optically imposed myopizing conditions; and/or
  the myopia inducing conditions are proximal environment imposed myopizing conditions; and/or
  during the myopia condition step the wearer carries out near vision tasks; and/or
  the myopia condition step is carried out during at least 1 minute prior to the resulting myopia indicator determining step; and/or
  the myopia condition step is carried out during at most 60 minutes prior to the resulting myopia indicator determining step; and/or
  the myopia control product is selected among the list consisting of: myopia control ophthalmic lenses, myopia control contact lenses, myopia control optical lenses, myopia control drugs, optical system having a specific transmission pattern.

Another aspect of the invention relates to a method for selecting a myopia control product for a wearer among a list of myopia control products, comprising evaluating the efficiency of each myopia control device for the wearer using a method according to the invention and selecting the most efficient myopia control product.

According to further embodiments which can be considered alone or in combination:
  the method further comprises a resting step between each efficiency evaluation during which the wearer rests until the value of the myopia indicator of the wearer is close to the initial value of the myopia indicator of the wearer; and/or
  during the resting step the wearer is subject to bright light and/or to myopic defocus and/or carries out far vision tasks; and/or
  the same myopia inducing condition is used for evaluating each myopia control product.

According to a further aspect, the invention relates to a computer program product comprising one or more stored sequences of instructions that are accessible to a processor and which, when executed by the processor, causes the processor to carry out the steps of the method according to an embodiment of the invention.

Another aspect of the invention relates to a computer readable medium carrying one or more sequences of instructions of the computer program product according to an embodiment of the invention.

Another aspect of the invention relates to a program which makes a computer execute the method according to an embodiment of the invention.

Another aspect of the invention relates to a computer-readable storage medium having a program recorded thereon; where the program makes the computer execute the method according to an embodiment of the invention.

Another aspect of the invention relates to a device comprising a processor adapted to store one or more sequence of instructions and to carry out at least one of the steps of the method according to an embodiment of the invention.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Non limiting embodiments of the invention will now be described with reference to the accompanying drawing in which.

DETAILED DESCRIPTION OF THE DRAWINGS

Figure 1:
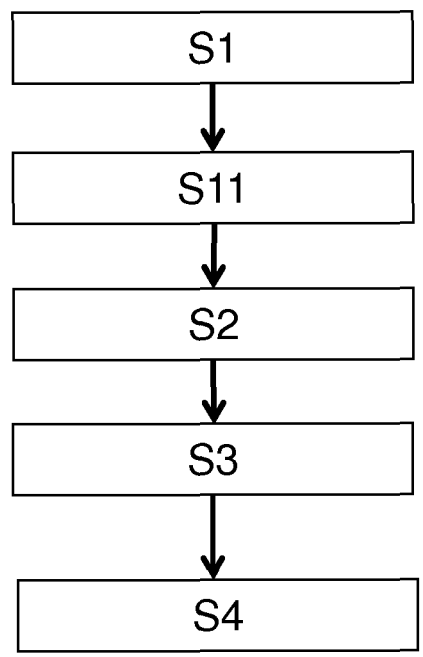
FIG. 1 is a flowchart of the step of a method according to the invention.

As illustrated on FIG. 1, the method according to the invention comprises:

an initial myopia indicator providing step S1,
a myopia condition step S2,
a resulting myopia indicator determining step S3,
an efficiency evaluation step S4.

The initial value of a myopia indicator of the wearer is provided during the initial myopia indicator providing step S1.

The myopia indicator may be of any type of indicator that may be related to myopia progression and whose value may change in a relatively short period of time, for example in less than 1 hour, preferably less than 30 minutes, when the wearer is placed in myopia inducing conditions.

The myopia indicator may advantageously be a parameter related to the axial length of the wearer's eyes or the thickness of the wearer's choroid. Indeed, the inventor have observed that such indicators can be related to myopia progression of the wearer and that changes in the values of such indicators can be measured within a short period of time, less that 30 minutes when the wearer is placed in myopia induced conditions.

Such indicators may be measured using well known commercial devices, such as Zeiss IOLMaster, Haag-Strit Lenstart LS 900 or optical coherence tomography.

Other myopia indicators may be used, for example subjective and/or objective refraction or lens thickness.

The myopia indicator may be measured only on one eye of the wearer or may correspond to the average value or greatest or smallest or difference of values when measured on both eyes of the wearer.

The initial value of the myopia indicator corresponds to the value of the myopia indicator before the wearer has been provided with a myopia control product and before the wearer has been placed in myopia inducing condition.

For example, the initial value of the myopia indicator may be measured on the wearer after the wearer has been subject to bright light and/or to myopic defocus and/or has carried out far vision tasks. For example the wearer may have been asked to walk out doors for 15 to 30 minutes before the initial value of the myopia indicator is measured.

According to an embodiment of the invention, the initial value of the myopia may have been measured previously and stored in a data base. The eye care professional may access to the data base to retrieve the initial value.

According to an embodiment of the invention, the method may further comprise a myopia control product providing step S11. The myopia control product whose efficiency is to be measured is provided during the myopia control product providing step S11.

The myopia control product may be selected among the list consisting of: myopia control ophthalmic lenses, myopia control contact lenses, myopia control optical lenses, myopia control drugs, optical system having a specific transmission pattern.

Among the drugs that may be used as myopia control product, some are in the form of drops to be put in the eyes of the wearer, for example Atropine or Pirenzepine, others may be pills such as 7-Methylxanthine.

Among the contact lenses that may be used as myopia control product one may use multifocal contact lenses such a MiSight from Cooper Vision or orthokeratologic contact lenses.

Bifocal ophthalmic lenses may be used as myopia control product. Progressive multifocal ophthalmic lenses may also be used to slow down myopia progression, for example Myopilux Pro from Essilor, SOLA MC from Zeiss, View Cola form Hoya, Dr. Somo from Somo, kids pro from Swissvoat, KidsFM from ILT, GIA Kids from American Polylite.

Prismatic bifocal lenses may also be cited as example of myopia control ophthalmic lens, for example Myopilux Max from Essilor or Hanlin from Tangram.

Near vision Single vision lenses with horizontal prism may also be used to slow down myopia progression, such as CME from Wanxin.

Periphery correction lenses may be used such as disclosed in U.S. Pat. No. 7,976,158.

Optical system having a specific transmission pattern may be used to slow down myopia progression. For example such optical system may have a transmission pattern comprising at least a first zone Z1 extending from 380 nm to a first limit L1 between the first zone Z1 and a second zone Z2, and a third zone Z3 extending from a second limit L2 between the second zone Z2 and the third zone Z3 to 780 nm, wherein the first limit L1 is greater than or equal to 436 nm and the second limit L2 is greater than the first limit L1 and smaller than or equal to 487 nm; the average transmission values T1, T2, T3, in each zone Z1, Z2, Z3 are such as:

$$T2 > (T1+T3)/2, \text{ with}$$

T1 the average transmission over the first zone Z1,
T2 the average transmission over the second zone Z2, and
T3 the average transmission over the third zone Z3,
T1 and T3 being greater than or equal to 3% and smaller than or equal to 70%.

Further features of such optical system are disclosed in EP 13305237.

As illustrated by the above cited examples of myopia control product, there is a need for a method to evaluate the efficiency in terms of myopia control of the different products for a given wearer.

According to an embodiment of the invention, the myopia control product provided during the myopia control product providing step may be the wearer's usual distance correction. Advantageously, such embodiment may be used to demonstrate to the wearer the usefulness of the myopia control device by comparing the myopia progression of the wearer's usual distance correction with the myopia progression when using a myopia control product.

The wearer using a myopia control product to be tested is placed in myopia inducing conditions during the myopia condition step S2.

Myopia inducing conditions are to be understood as conditions, for example visual conditions, that cause a myopia increase greater than the usual visual conditions of the wearer.

The myopia inducing conditions may be optically imposed myopizing conditions.

According to an embodiment of the invention, the myopia inducing conditions are proximal environment imposed myopizing conditions, such as an environment that imposes a near environment in all directions. For example during the myopia condition step S2, the wearer may carry out near vision tasks, for example read, write, or use a netbook or a smartphone.

Advantageously, the wearer should be left in the myopia inducing conditions for a period of time long enough to create a measureable change in the myopia indicator. For example the myopia conditions step S2 may be carried out during at least 1 minute, for example during at least 10 minutes.

The myopia conditions step S2 should not last too long so as to allow testing different types of myopia control product.

For example the myopia control step S2 may be carried out during at most 60 minutes, for example during at most 30 minutes.

Figure 2:
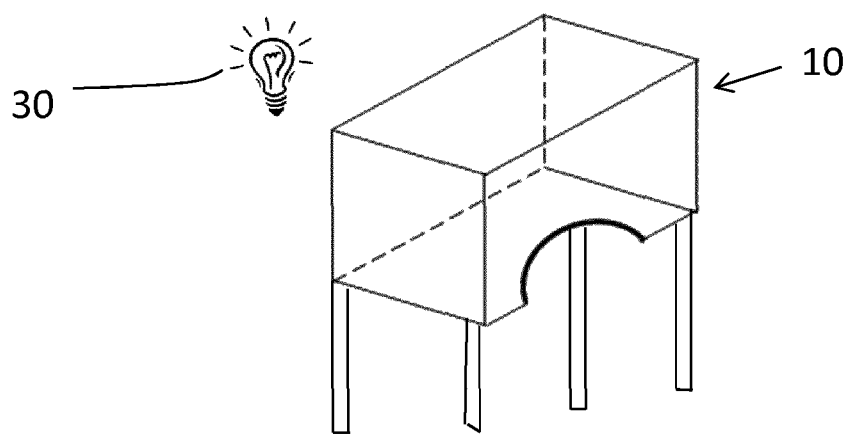
FIG. 2 is an example of a myopia inducing environment

An example of myopizing environment is illustrated on FIG. 2. As represented on FIG. 2, the visual space of the wearer is restricted to proximal environment in all directions by the use of a cubicle environment 10.

Although in the example of FIG. 2, the environment is represented as cubicle, the skilled person will understand that the cubicle may have other shapes such as spherical or cylindrical.

In the example of FIG. 2, the wearer undergoes a near vision task within the cubicle environment 10 with an external light source 30.

The lighting in the environments can be adjusted to promote myopization for example using low light or red light spectrum. The lighting may also be increased in order to test solar lenses. For this purpose, the walls of the cubicle/cylinder/sphere should be translucent, light source (s) 30 being placed behind. Moreover, in order to further promote myopization, the walls can contain specific patterns, such as black and white stripes or checkerboard.

The advantage of such environments is that they allow testing of any myopia control lens, for example color filters, progressive addition, bifocals or peripheral correction lenses, because the wearer can modify its posture depending on the needs of the task. The testing of progressive addition lenses for myopia control better explains this advantage: the efficacy of progressive addition lenses for myopia control depends of the use of its near vision zone by the wearer. If the wearer reads while using the far vision part of the lens, the myopia control effect will be null. In this kind of environment, the wearer can adopt its natural posture and either use or not the near vision zone of the progressive addition lenses for its task, which will therefore influence the outcome of the myopia control indicator.

Tasks in this environment can be any near task, such as reading, writing, hand held video game playing etc.

Figure 3:
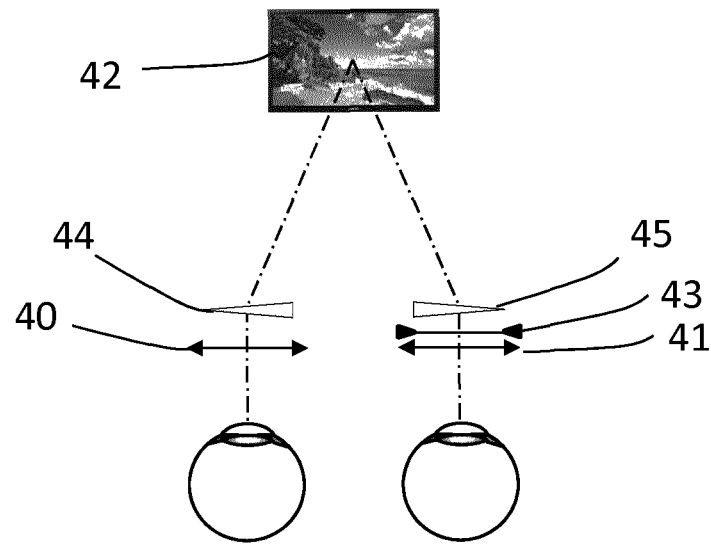
FIG. 3 is a further example of myopia inducing environment.

The myopia inducing conditions may be optically imposed myopizing conditions as illustrated on FIG. 3.

Such kind of set-up reproduces well known myopizing conditions by imposing monocular hyperopic defocus on one of the wearer's eyes.

The device is advantageously composed of two collimators 40, 41 optically focusing the display 42 at infinity to reduce bulkiness. In another embodiment, there could be no collimators with the image placed far from the wearer, for example 5 m. A defocus lens 43, for example a negative lens, for example of −3.00 D, induces hyperopic defocus, which is a known myopizing stimulus. In another embodiment, the defocus lens could be replaced by a diffuser or a positive lens. A pair of base-in prisms 44 and 45 can also be added to compensate convergence if the display is close.

Figure 4:
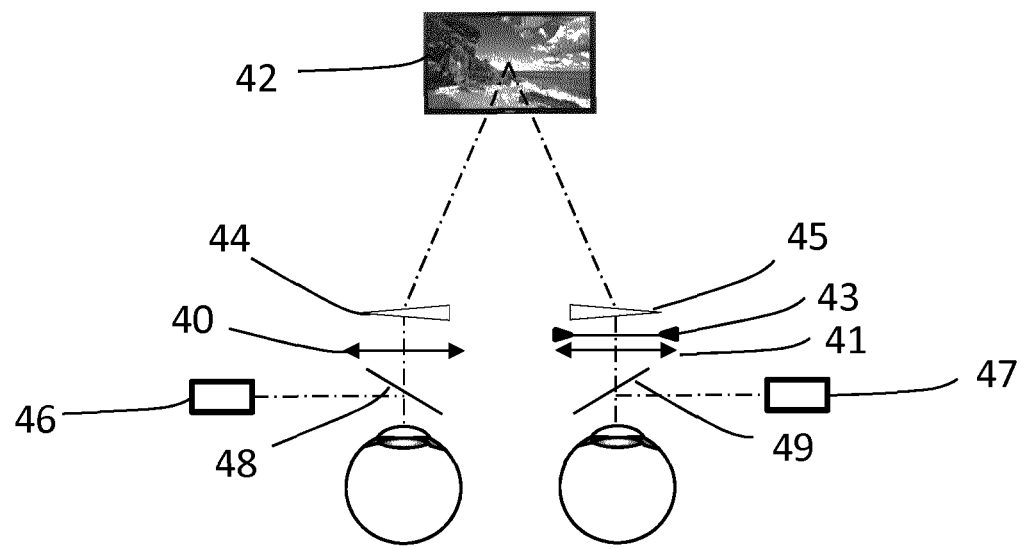
FIG. 4 is an additional example of myopia inducing environment.

Advantageously, as illustrated on FIG. 4, the myopia inducing conditions may also contain measurement devices 46, 47 used for the initial and resulting myopia indicator measurements, for example by means of beam splitters 48, 49. This embodiment allows a direct measurement of the myopia inducing effect on the eye during the myopia condition step S2. Indeed, by measuring the myopia indicator directly during the myopia condition step S2, one makes sure that the myopia indicator is not affected by the time to bring the wearer from the myopia inducing condition to the measurement device. Moreover, by tracking the change of the myopia indicator, one can optimize the myopia inducing task length, based on a minimum change of the myopia indicator that is necessary to judge the effect of a myopia control product.

During the resulting myopia indicator determining step S3, the resulting value of the myopia indicator of the wearer is determined after the wearer has been placed in the myopia inducing conditions.

The efficiency of the myopia control product is evaluated during the efficiency evaluation step S4. Such efficiency may be evaluated by comparing the initial value of the myopia indicator and the resulting value of the myopia indicator. For example, the initial value of the myopia indicator may correspond to the value of the myopia indicator measured when the wearer uses his usual distance correction.

Such evaluations may be measured either on both eyes of the wearer or only on one of the wearer's eyes.

The invention further relates to a method of selecting a myopia control product for a wearer among a list of myopia control products. Such method comprises evaluating the efficiency of each myopia control device for the wearer using a method according to the invention and selecting the most efficient myopia control product.

While selecting the most efficient myopia control product, other criteria that the myopia control efficiency may be considered, for example the price of the product or the use constraints of the product or the side effects of the product.

Preferably the same myopia inducing condition is used for evaluating each myopia control product.

According to a preferred embodiment of the invention, the method for selecting a myopia control product further comprises a resting step between each efficiency evaluation during which the wearer rests until the value of his myopia indicator is close to the initial value of the myopia indicator of the wearer. For example the wearer rests until the difference between the effective value of his myopia indicator and the initial value of his myopia indicator is smaller than 20%.

So as to reduce the resting time, during the resting step the wearer may be subject to bright light and/or to myopic defocus and/or carries out far vision tasks.

Example 1

The inventors have carried out the method according to the invention using myopia inducing conditions as illustrated on FIG. 2 to help a child select among different myopia control products.

To start with, axial length of the child's both eyes is measured, using a Zeiss IOLMaster. The measured values are OD: 25.785 mm/OS: 25.642 mm.

The method is carried out in a cubical ecological myopizing environment as illustrated on FIG. 2. In normal conditions of usage, the walls of this environment are never further than 50 cm from the child's eyes.

First progressive addition lenses with an addition of +1.50 D are tested. The child has plano progressive addition lenses with an addition of +1.50 D added to its spectacles, using clip-ons. The child is placed in the myopizing environment for 10 minutes and asked to read the latest Harry Potter book. Once this time is over, its axial length is measured again: OD: 25.796 mm/OS: 25.651 mm.

For the time spent, the indicator and the type of myopizing environment, it is considered that 0.005 mm is a threshold to achieve decent myopia control. As both eyes elongated by more than 0.005 mm (OD: +0.011 mm/OS: +0.009 mm), the progressive addition lenses are rejected, perhaps because during reading, the child lowered the head rather than the eyes and therefore did not use the near vision part of the lens.

The child is given a 15 minutes rest to allow his eyes to come back to its original state.

After such resting step, axial length is measured again: OD: 25.786 mm/OS: 25.644 mm.

This time, a filter as described above is used (Z132 [390,446] nm, Z2=[446,477] nm, Z3=[477,780] nm, T1=42%, T2=96%, T3=38%). The child continues to read the Harry Potter book for 10 more minutes. Once this time is over, its axial length is measured again: OD: 25.790 mm/OS: 25.647 mm. The change in axial length is lower than the 0.005 mm threshold (OD: +0.004 mm/OS: +0.003 mm); the filter is chosen.

Example 2

The inventors have carried out the method according to the invention using myopia inducing conditions as illustrated on FIG. 3 to help a child select among the different myopia control products.

To begin with, choroidal thickness of both eyes of the child is measured, using OCT. The initial values are OD: 293 nm/OS: 307 nm, with therefore an OD-OS difference of −14 nm.

A monocular defocus inducer as illustrated on FIG. 3 is used, containing a −3.00 D defocus lens on the left eye. The collimators are +2.5 D lenses, the screen is placed at 40 cm of the collimators. To relieve convergence, the system also contains 2 base-in prisms of 7.5 prismatic diopters each.

The child watches 5 minutes of a Mister Bean movie, wearing its usual distance prescription and a binocular filter with the following parameters: Z1=[390,446] nm, Z2=[446, 477] nm, Z3=[477,780] nm, T1=42%, T2=85%, T3=38%. After that, choroidal thickness is measured again: OD: 292 nm/OS: 295 nm. The difference between the right and the left eye is −3 nm, i.e. an increase of 11 nm compared to the initial measurement. As the threshold for this device is an increase of 5 nm, the filter is rejected.

After a period of 3 minutes rest, the choroidal thickness is measured again: OD: 294 nm/OS: 308 nm, with therefore an OD-OS difference of −14 nm.

This time, the child tries a binocular filter with the following properties (and a higher cost): Z1=[390,446] nm, Z2=[446,477] nm, Z3=[477,780] nm, T1=0.38, T2=0.96, T3=0.45. After 5 more minutes of Mister Bean, choroidal thickness is measured again: OD: 296 nm/OS: 307 nm. The difference between the right and the left eye is −11 nm, i.e. an increase of 3 nm compared to the initial measurement. As the threshold for this device is an increase of 5 nm, the filter is chosen, even if it is more expensive.

The invention further relates to a method of selling a myopia control product.

According to an aspect of the invention, such method comprises the steps of selecting a myopia control product among a list of myopia control product using the method according to the invention and a step of selling the most efficient myopia control product to the wearer.

According to further aspect of the invention, such method comprises the steps of demonstrating the efficiency of a myopia control device to a wearer by a method according to the invention and a step of selling said myopia control device to the wearer.

The invention has been described above with the aid of embodiments without limitation of the general inventive concept.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. A method of evaluating the efficiency of a myopia control product for a wearer, the method comprising:
   an initial myopia indicator providing step S1, during which the initial value of a myopia indicator of the wearer is provided;
   a myopia condition step S2, during which the wearer using a myopia control product is placed in myopia inducing conditions, myopia inducing conditions being conditions that cause a myopia increase greater than usual visual conditions of the wearer;
   a resulting myopia indicator determining step S3, during which the resulting value of the myopia indicator of the wearer is determined after the wearer has been placed in the myopia inducing conditions; and
   an efficiency evaluation step S4, during which the efficiency of the myopia control product is evaluated by comparing the initial value of the myopia indicator and the resulting value of the myopia indicator.

2. The method according to claim 1, wherein the myopia indicator is a parameter related to the axial length of the wearer's eyes or the thickness of the wearer's choroid.

3. The method according to claim 1, wherein the myopia control product is the wearer's usual distance correction.

4. The method according to claim 1, wherein the myopia inducing conditions are optically imposed myopizing conditions.

5. The method according to claim 1, wherein the myopia inducing conditions are proximal environment imposed myopizing conditions.

6. The method according to claim 1, wherein during the myopia condition step the wearer carries out near vision tasks.

7. The method according to claim 1, wherein the myopia condition step is carried out during at least 1 minute prior to the resulting myopia indicator determining step.

8. The method according to claim 1, wherein the myopia condition step is carried out during at most 60 minutes prior to the resulting myopia indicator determining step.

9. The method according to claim 1, wherein the myopia control product is selected among the list consisting of: myopia control ophthalmic lenses, myopia control contact lenses, myopia control optical lenses, myopia control drugs, optical system having a specific transmission pattern.

10. A method for selecting a myopia control product for a wearer among a list of myopia control products, comprising evaluating the efficiency of each myopia control device for the wearer using a method according to claim 1 and selecting the most efficient myopia control product.

11. The method according to claim 10, wherein the method further comprises a resting step between each efficiency evaluation during which the wearer rests until the value of the myopia indicator of the wearer is close to the initial value of the myopia indicator of the wearer.

12. The method according to claim 11, wherein during the resting step the wearer is subject to bright light and/or to myopic defocus and/or carries out far vision tasks.

13. The method according to claim 10, wherein the same myopia inducing condition is used for evaluating each myopia control product.

14. A non-transitory computer program product comprising one or more stored sequences of instructions that are accessible to a processor and which, when executed by the processor, causes the processor to carry out the steps of claim 1.

15. A non-transitory computer readable medium carrying one or more sequences of instructions of the non-transitory computer program product of claim 14.

* * * * *